United States Patent
Vernon

(10) Patent No.: US 7,772,250 B2
(45) Date of Patent: Aug. 10, 2010

(54) COMPOUNDS

(75) Inventor: Lois Elizabeth Vernon, Stevenage (GB)

(73) Assignee: Theravance, Inc., South San Francisco, CA (US)

( * ) Notice: Subject to any disclaimer, the term of this patent is extended or adjusted under 35 U.S.C. 154(b) by 1250 days.

(21) Appl. No.: 11/327,886

(22) Filed: Jan. 9, 2006

(65) Prior Publication Data

US 2006/0189654 A1   Aug. 24, 2006

Related U.S. Application Data

(60) Provisional application No. 60/642,844, filed on Jan. 11, 2005.

(51) Int. Cl.
*A61K 31/04* (2006.01)
*C07D 215/38* (2006.01)
(52) U.S. Cl. .................. 514/314; 546/159; 546/153
(58) Field of Classification Search ............ 546/153, 546/159; 514/314
See application file for complete search history.

(56) References Cited

U.S. PATENT DOCUMENTS

| 6,653,323 | B2 | 11/2003 | Moran et al. | |
| 6,670,376 | B1 | 12/2003 | Moran et al. | |
| 6,949,568 | B2 | 9/2005 | Moran et al. | |
| 7,060,712 | B2 | 6/2006 | Axt et al. | |
| 7,317,023 | B2 * | 1/2008 | McKinnell et al. | 514/312 |
| 7,399,863 | B2 | 7/2008 | Linsell | |
| 2003/0229058 | A1 | 12/2003 | Moran et al. | |
| 2005/0159448 | A1 * | 7/2005 | McKinnell et al. | 514/312 |
| 2008/0125462 | A1 * | 5/2008 | Vernon | 514/312 |

FOREIGN PATENT DOCUMENTS

| WO | 03/042164 A | 5/2003 |
| WO | 2005/070872 A | 8/2005 |

* cited by examiner

*Primary Examiner*—D. Margaret Seaman
(74) *Attorney, Agent, or Firm*—Jeffrey A. Hagenah; Roberta P. Saxon

(57) ABSTRACT

This invention relates to cinnamate salts of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

18 Claims, 5 Drawing Sheets

COMPOUNDS

The present application claims priority to U.S. provisional application Ser. No. 60/642,844 and UK application nos. 0514199.8, 0514200.5 and 0500513.7 respectively filed Jan. 11, 2005, Jul. 11, 2005, Jul. 11, 2005 and Jan. 11, 2005, the disclosures of which are incorporated herein by reference in their entirety.

The present invention relates to novel salts of a $\beta_2$ adrenergic agonist. In particular the invention relates to novel crystalline salts of compound (A) defined below. In addition the invention provides a process for preparing said crystalline salts of compound (A) and to pharmaceutical compositions containing them and their use in medicine.

$\beta_2$ Adrenergic receptor agonists are recognized as effective drugs for the treatment of pulmonary diseases such as asthma and chronic obstructive pulmonary disease (including chronic bronchitis and emphysema). $\beta_2$ Adrenergic receptor agonists are also useful for treating premature labour, and are potentially useful for treating neurological disorders and cardiac disorders.

U.S. patent application Ser. No. 60/535,784, and U.S. 2005/0159448A1 describe compounds of formula:

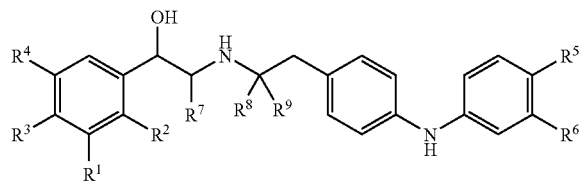

wherein:
each of $R^1$, $R^2$, $R^3$, and $R^4$ is independently selected from the group consisting of hydrogen, hydroxy, amino, halo, —CH$_2$OH and —NHCHO, or $R^1$ and $R^2$ taken together are selected from the group consisting of —NHC(=O)CH=CH—, —CH=CHC(=O)NH—, —NHC(=O)S; and —SC(=O)NH—;
one of $R^5$ and $R^6$ is —[X—C$_{1-6}$alkylenyl]$_n$-NR$^{10}$R$^{11}$ or C$_{1-6}$alkylenyl-NR$^{12}$R$^{13}$, and the other of $R^5$ and $R^6$ is selected from the group consisting of hydrogen, hydroxy, C$_{1-4}$alkoxy, and C$_{1-4}$alkyl, wherein C$_{1-4}$alkyl is optionally substituted with halo,
wherein
each X is independently selected from the group consisting of —O—, —NH—, —S—, —NHSO$_2$—, —SO$_2$NH—, —NHC(=O)—, and —C(=O)NH—;
each of $R^{10}$, $R^{11}$, $R^{12}$, and $R^{13}$ is independently hydrogen or C$_{1-4}$alkyl; or
$R^{10}$ and $R^{11}$, together with the nitrogen atom to which they are attached, or $R^{10}$, together with the nitrogen atom to which it is attached and a carbon atom of the adjacent C$_{1-6}$alkylenyl, or $R^{12}$ and $R^{13}$, together with the nitrogen atom to which they are attached, or $R^{12}$, together with the nitrogen atom to which it is attached and a carbon atom of the adjacent C$_{1-6}$alkylenyl, form a heterocyclic or heteroaryl ring having from 5 to 7 ring atoms, wherein the ring optionally contains an additional heteroatom selected from oxygen, nitrogen, and sulfur, wherein nitrogen is optionally substituted with —S(O)$_2$—C$_{1-4}$alkyl; and n is 1, 2, or 3; and
each of $R^7$, $R^8$, and $R^9$ is independently hydrogen or C$_{1-6}$alkyl;
and pharmaceutically-acceptable salts, solvates and stereoisomers thereof.

Compounds of the aforementioned US applications are said to be potent and selective $\beta_2$ adrenergic receptor agonists.

Example 1 of the aforementioned US applications is the compound: 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one (hereinafter referred to as Compound A), which may be depicted by the structural formula (I):

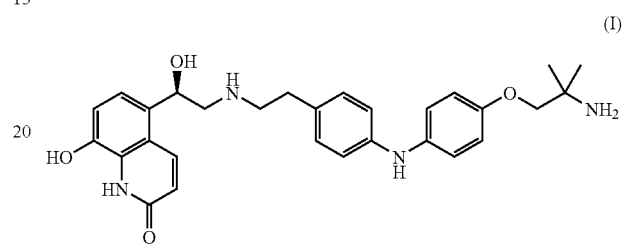

We have now found certain novel salts of Compound A, viz. the cinnamate, 4-methoxy cinnamate, 4-phenyl cinnamate and the 4-methyl cinnamate salts hereinafter known as the "salts of the invention".

In a first aspect therefore the present invention provides a salt of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one, selected from a cinnamate, 4-methoxycinnamate, di-(4-phenylcinnamate) and 4-methyl cinnamate salt.

The invention also provides a salt of the compound of formula (I) hereinabove, wherein said salt is selected from a cinnamate, 4-methoxycinnamate, di-(4-phenylcinnamate) and 4-methyl cinnamate salt.

In one embodiment the present invention provides a cinnamate salt of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

In another embodiment the present invention provides a 4-methoxy cinnamate salt of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

In a further embodiment the present invention provides a di-(4-phenylcinnamate) salt of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

In a further embodiment the invention provides a 4-methyl cinnamate salt of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

In a particular embodiment the invention provides a crystalline 4-methyl cinnamate salt of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

In a particular embodiment the invention provides a crystalline cinnamate salt of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

In another embodiment the invention provides a crystalline 4-methoxy cinnamate salt of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

In a particular embodiment the invention provides a crystalline di-(4-phenylcinnamate) salt of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

We have found that salts of the invention may have varying hydration states. In a further embodiment the present invention encompasses hydrates of salts of the invention. Thus, for example the 4-methycinnamate salt may be obtained as a dihydrate, or as a hydrate associated with 3.5 moles of water.

The present invention also encompasses solvates of salts of the invention.

Salts of the invention may also exist in different stoichiometries. Thus for example, the salt with 4-phenylcinnamic acid is formed with 2 moles of acid to each mole of Compound A.

It will be appreciated that the compound of formula (I), which is depicted and named as the R-isomer with respect to the OH group, may be in admixture with the corresponding S-isomer and hence salts of the invention may also exist as mixtures of said isomers. Thus for example, said admixture may contain at least 90%, for example at least 95% of the R-isomer.

The salts of the invention may be prepared by contacting a solution of compound A with an acid selected from cinnamic acid, 4-methoxy cinnamic acid, 4-phenylcinnamic acid or 4-methylcinnamic acid. Compound A may for example be dissolved in an aqueous organic solution, for example in a mixture of tetrahydrofuran and water, or an aqueous alcohol such as aqueous industrial methylated spirit. The reaction may be effected with stirring. The reaction temperature may be in the range from 0° C. to 50° C., for example from 15° C. to 30° C. Crystallisation may occur spontaneously or it may be induced, for example by scratching or seeding.

In one aspect of the present invention is provided a method for preparing a 4-methoxy cinnamate salt of Compound A which comprises contacting in solution Compound A and 4-methoxy cinnamic acid.

In another aspect the present invention provides a method for preparing a cinnamate salt of compound A which comprises contacting in solution Compound A and cinnamic acid.

In a further aspect the present invention provides a method for preparing a di-4-phenyl cinnamate salt of compound A which comprises contacting in solution Compound A and 4-phenylcinnamic acid.

In a yet further aspect the present invention provides a method for preparing a 4-methyl cinnamate salt of compound A which comprises contacting in solution Compound A and 4-methyl cinnamic acid.

Compound A may itself be prepared using one of the general methods described in U.S. Patent Application No. 60/535,784, and US 2005/0159448A1 as described hereinafter. Compound A may also be prepared by the specific method described by the Reference Example hereinafter.

The aforementioned US patent applications describes inter alia the following general methods for the preparation of compounds defined therein:

General Synthetic Procedures

Compounds of U.S. patent application No. 60/535,784, and US 2005/0159448A1 can be prepared from readily available starting materials using the following general methods and procedures.

As will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

In one method of synthesis, compounds are prepared as illustrated in Scheme A. (The substituents and variables shown in the following schemes have the definitions provided above unless otherwise indicated.)

Scheme A

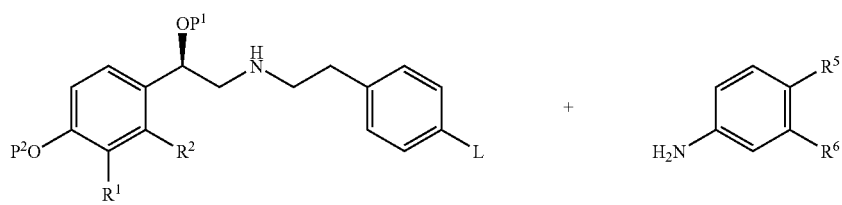

-continued

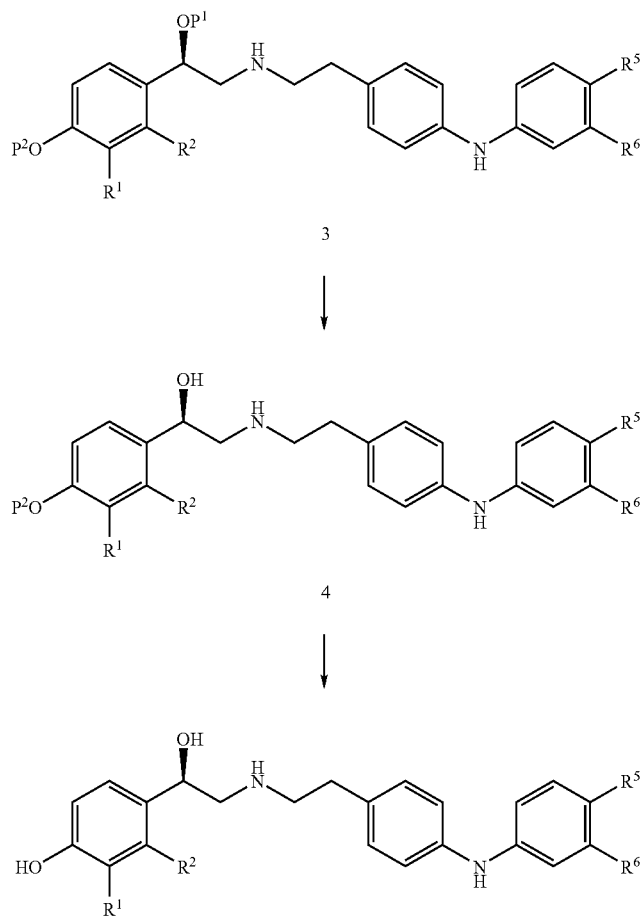

where $P^1$ represents a hydroxy-protecting group, $P^2$ represents a hydroxy-protecting group, and L represents a leaving group, such as bromo.

As shown in Scheme A, a compound of formula 1 is first reacted with an aryl amine (2) to provide an intermediate of formula 3. Typically, this reaction is conducted in an organic solvent in the presence of base and a transition metal catalyst and arylphosphine ligand with heating. A useful catalyst for coupling of an aryl group to an aryl amine is tris(dibenzylidenacetone)dipalladium(0) together with rac-2,2'-bis(diphenylphosphino)-1,1'-binapthyl. The reaction is typically heated at a temperature of between about 50° C. and about 120° C. for between about 0.25 and about 12 hours.

The protecting group $P^1$ is typically a silyl protecting group, which is typically removed from the intermediate of formula 3 using a fluoride or acid reagent, to provide an intermediate of formula 4. The protecting group $P^2$ is typically a benzyl protecting group, which is typically removed from the intermediate of formula 4 by hydrogenation using a palladium on carbon catalyst, to provide the product.

An alternative method of preparing intermediate 3 is illustrated in Scheme B.

Scheme B

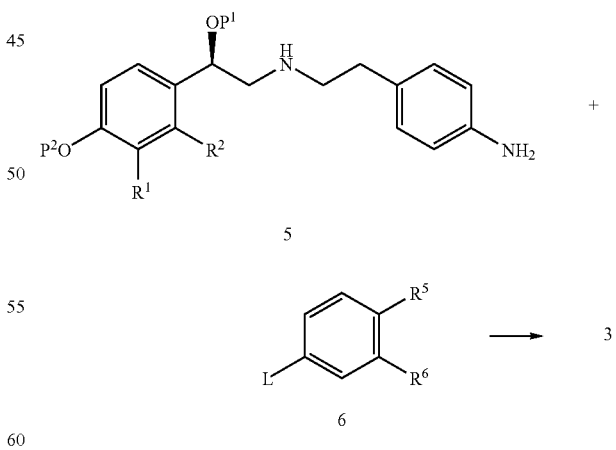

The conditions for the coupling of intermediates 5 and 6 in Scheme B to produce intermediate 3 are typically the same as those used to couple intermediates 1 and 2 in Scheme A.

Yet another alternative method of preparing intermediate 3 is illustrated in Scheme C.

Scheme C

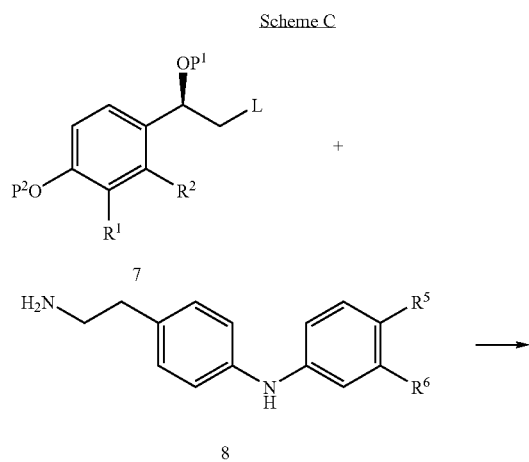

The reaction of Scheme C is typically conducted in a aprotic solvent in the presence of base. Typical suitable solvents include dimethylsulfoxide, dimethyl formamide, dimethylacetamide and the like. The reaction is typically heated at a temperature of between about 60° C. and about 140° C. for between about 0.25 and about 4 hours.

The compounds of formula 1 and 7 employed in the reactions described in this application are readily prepared by procedures known in the art, and described, for example, in U.S. Pat. Nos. 6,653,323 B2 and 6,670,376 B1, which are incorporated herein by reference, and references therein. Intermediate 5 can be prepared by reaction of intermediate 7 with 2-(4-aminophenyl)ethylamine in an aprotic solvent with heating.

Intermediates 2 and 6 are available commercially or are prepared from readily available starting materials. For example, when $R^5$ is —[O—$C_{1-6}$alkylenyl]n-NR$^{10}$R$^{11}$ and $R^6$ is hydrogen, intermediate 2', of general formula 2, can be prepared by the process of Scheme D

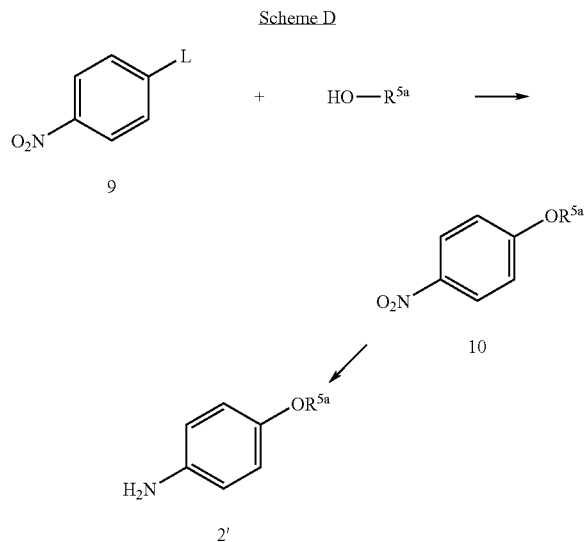

where $R^{5a}$ is defined such that —$OR^{5a}$ is —[O—$C_{1-6}$alkylenyl]n-NR$^{10}$R$^{11}$. As one example of suitable reaction conditions for Scheme D, the reaction is conducted in dimethylsulfoxide in the presence of sodium hydride. Alternatively, the reaction of intermediate 9 with the compound HO—$R^{5a}$ may be conducted in a solvent such as tetrahydrofuran, in the presence of a base such as potassium tert.-butoxide. Intermediate 10 may be converted into Intermediate 2' by hydrogenation, for example using palladium on charcoal, in a solvent such as industrial methylated spirits.

Further details regarding specific reaction conditions and other procedures for preparing Compound A are described in the Examples and Reference Example below.

As indicated hereinabove compounds of U.S. patent application No. 60/535,784, and US 2005/0159448A, including Compound A, are potent and selective $\beta_2$ adrenergic receptor agonists. The present invention accordingly also provides a method for the prophylaxis or treatment of a clinical condition in a mammal, such as a human, for which a selective $\beta_2$-adrenoreceptor agonist is indicated, which comprises administration of a therapeutically effective amount of a salt of the this invention. In particular, the present invention provides such a method for the prophylaxis or treatment of a disease associated with reversible airways obstruction such as asthma, chronic obstructive pulmonary disease (COPD), respiratory tract infection or upper respiratory tract disease. In a further aspect the present invention provides such a method for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

In the alternative, there is also provided a salt of the invention for use in medical therapy, particularly, for use in the prophylaxis or treatment of a clinical condition in a mammal, such as a human, for which a selective $\beta_2$-adrenoreceptor agonist is indicated. In particular, there is provided a salt of the invention for the prophylaxis or treatment of a disease associated with reversible airways obstruction such as asthma, chronic obstructive pulmonary disease (COPD), respiratory tract infection or upper respiratory tract disease. In a further aspect, there is provided a salt of the invention for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

The present invention also provides the use of a salt of the invention in the manufacture of a medicament for the prophylaxis or treatment of a clinical condition for which a selective $\beta_2$-adrenoreceptor agonist is indicated, for example a disease associated with reversible airways obstruction such as asthma, chronic obstructive pulmonary disease (COPD), respiratory tract infection or upper respiratory tract disease. In a further aspect, there is provided a salt of the invention in the manufacture of a medicament for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

The amount of a salt of the invention which is required to achieve a therapeutic effect will, of course, vary with the route of administration, the subject under treatment, and the particular disorder or disease being treated. Salts of the invention may be administered by inhalation at a dose of from 0.0005 mg to 10 mg, preferably from 0.005 mg to 0.5 mg, for example, from 0.05 mg to 0.5 mg. The dose range for adult humans is generally from 0.0005 mg to 10 mg per day and preferably from 0.01 mg to 1 mg per day, most preferrably from 0.05 mg to 0.5 mg.

While it is possible for a salt of the present invention, selected from Compound A cinnamate, Compound A 4-methoxycinnamate, Compound A di-(4-phenylcinnamate) and Compound A 4-methylcinnamate, to be administered alone, it is preferable to present it as a pharmaceutical formulation.

Accordingly, the present invention provides a pharmaceutical formulation comprising Compound A cinnamate, and a pharmaceutically acceptable carrier or excipient, and optionally one or more other therapeutic ingredients.

The present invention provides a pharmaceutical formulation comprising Compound A 4-methoxycinnamate, and a pharmaceutically acceptable carrier or excipient, and optionally one or more other therapeutic ingredients.

The present invention further provides a pharmaceutical formulation comprising Compound A di-(4-phenyl cinnamate), and a pharmaceutically acceptable carrier or excipient, and optionally one or more other therapeutic ingredients.

The present invention further provides a pharmaceutical formulation comprising Compound A 4-methyl cinnamate, and a pharmaceutically acceptable carrier or excipient, and optionally one or more other therapeutic ingredients.

The formulations include those suitable for oral, parenteral (including subcutaneous, intradermal, intramuscular, intravenous and intraarticular), inhalation (including fine particle dusts or mists which may be generated by means of various types of metered dose pressurised aerosols, nebulisers or insufflators), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing a salt of the invention (hereinafter also referred to as 'active ingredient') into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Dry powder compositions for topical delivery to the lung by inhalation may, for example, be presented in capsules and cartridges of for example gelatine, or blisters of for example laminated aluminium foil, for use in an inhaler or insufflator. Powder blend formulations generally contain a powder mix for inhalation of the active ingredient and a suitable powder base (carrier/diluent/excipient substance) such as mono-, di or poly-saccharides (eg. lactose or starch). Use of lactose is preferred. Dry powder compositions may also include, in addition to the drug and carrier, a further excipient such as a sugar ester e.g. cellobiose octaacetate, calcium stearate or magnesium stearate.

Each capsule or cartridge may generally contain between 20 μg to 10 mg of a salt of the invention optionally in combination with another therapeutically active ingredient. Alternatively, the compound of the invention may be presented without excipients. Packaging of the formulation may be suitable for unit dose or multi-dose delivery. In the case of multi-dose delivery, the formulation can be pre-metered (eg as in Diskus, see GB 2242134, U.S. Pat. Nos. 6,632,666, 5,860,419, 5,873,360 and 5,590,645 or Diskhaler, see GB 2178965, 2129691 and 2169265, U.S. Pat. Nos. 4,778,054, 4,811,731, 5,035,237, the disclosures of which are hereby incorporated by reference) or metered in use (eg as in Turbuhaler, see EP 69715 or in the devices described in U.S. Pat. No. 6,321,747 the disclosures of which are hereby incorporated by reference). An example of a unit-dose device is Rotahaler (see GB 2064336 and U.S. Pat. No. 4,353,656, the disclosures of which are hereby incorporated by reference). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a salt of the invention preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet. Alternatively, the formulation may be presented if desired together with one or more other therapeutic agents in an inhalation device wherein the individual therapeutic agents are administrable simultaneously but are stored separately (or wholly or partly stored separately for triple combinations), e.g. in separate pharmaceutical compositions, for example as described in WO 03/061743.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain a salt of the invention optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetrafluoroethane, especially 1,1,1, 2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants e.g. oleic acid or lecithin and cosolvents e.g. ethanol. Pressurised formulations will generally be retained in a canister (e.g. an aluminium canister) closed with a valve (e.g. a metering valve) and fitted into an actuator provided with a mouthpiece.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means e.g. by micronisation. The desired fraction may be separated out by air classification or sieving. Preferably, the particles will be crystalline. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not more than 15% will have a MMD of less than 15 μm.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The salts of the invention may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose an acacia.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds and pharmaceutical formulations according to the invention may be used in combination with or include one or more other therapeutic agents, for example selected from anti-inflammatory agents, anticholinergic agents (particularly an $M_1$, $M_2$, $M_1/M_2$ or $M_3$ receptor antagonist), other $\beta_2$-adrenoreceptor agonists, antiinfective agents (e.g. antibiotics, antivirals), or antihistamines. The invention thus provides, in a further aspect, a combination comprising a salt of the invention together with one or more other therapeutically active agents, for example selected from an anti-inflammatory agent (for example a corticosteroid or an NSAID), an anticholinergic agent, another $\beta_2$-adrenoreceptor agonist, an antiinfective agent (e.g. an antibiotic or an antiviral), or an antihistamine. Examples of combinations are those comprising a salt of the invention together with a corticosteroid, and/or an anticholinergic, and/or a PDE-4 inhibitor. Suitable combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

Examples of anti-inflammatory agents include corticosteroids and NSAIDs. Corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, $6\alpha,9\alpha$-difluoro-$17\alpha$-[(2-furanylcarbonyl)oxy]-$11\beta$-hydroxy-$16\alpha$-methyl-3-oxo-androsta-1,4-diene-$17\beta$-carbothioic acid S-fluoromethyl ester, $6\alpha,9\alpha$-difluoro-$11\beta$-hydroxy-$16\alpha$-methyl-3-oxo-$17\alpha$-propionyloxy-androsta-1,4-diene-$17\beta$-carbothioic acid S-(2-oxo-tetrahydro-furan-3S-yl)ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, $6\alpha,9\alpha$-difluoro-$11\beta$-hydroxy-$16\alpha$-methyl-$17\alpha$-[(4-methyl-1,3-thiazole-5-carbonyl)oxy]-3-oxo-androsta-1,4-diene-$17\beta$-carbothioic acid S-fluoromethyl ester and $6\alpha,9\alpha$-difluoro-$17\alpha$-[(2-furanylcarbonyl)oxy]-$11\beta$-hydroxy-$16\alpha$-methyl-3-oxo-androsta-1,4-diene-$17\beta$-carbothioic acid S-fluoromethyl ester, more preferably $6\alpha,9\alpha$-difluoro-$17\alpha$-[(2-furanylcarbonyl)oxy]-$11\beta$-hydroxy-$16\alpha$-methyl-3-oxo-androsta-1,4-diene-$17\beta$-carbothioic acid S-fluoromethyl ester.

Examples of NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists) or inhibitors of cytokine synthesis.

Other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

A salt of the invention may be used in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

A method for determining $IC_{50}$ ratios is set out in U.S. Pat. No. 5,998,428 which is incorporated herein in full by reference as though set out herein. See also PCT application WO 00/51599 for another description of said assay.

Particular PDE4 inhibitors are those which have an $IC_{50}$ ratio of greater than 0.5, and particularly those compounds having a ratio of greater than 1.0. Examples of compounds include cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]; these are examples of compounds which bind preferentially to the low affinity binding site and which have an $IC_{50}$ ratio of 0.1 or greater.

Other Compounds of Interest Include:

Compounds set out in U.S. Pat. No. 5,552,438 issued 3 Sep. 1996; this patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (also known as cilomalast) and its salts, esters, pro-drugs or physical forms.

Other compounds of interest include AWD-12-281 from elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P. 2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T440 (Tanabe Seiyaku; Fuji, K. et al. J Pharmacol Exp Ther, 1998, 284(1): 162), and T2585.

Other possible PDE4 and mixed PDE3/PDE4 inhibitors include those listed in WO01/13953, the disclosure of which is hereby incorporated by reference.

Examples of anticholinergic agents are those compounds that act as antagonists at the muscarinic receptor, in particular those compounds which are antagonists of the $M_1$ and $M_2$ receptors. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-5148-1 (anhydrous form), atropine sulfate—CAS-5908-99-6; atropine oxide—CAS-4438-22-6 or its HCl salt—CAS-4574-60-1 and methylatropine nitrate—CAS-52-88-0.

Homatropine—CAS-87-00-3, hydrobromide salt—CAS-51-56-9, methylbromide salt—CAS-80-49-9.

Hyoscyamine (d, l)—CAS-101-31-5, hydrobromide salt—CAS-306-03-6 and sulfate salt—CAS-6835-16-1.

Scopolamine—CAS-51-34-3, hydrobromide salt—CAS-6533-68-2, methylbromide salt—CAS-155-41-9.

Particular anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Examples of antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, have a core structure, which can be represented by the following formula:

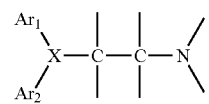

This generalized structure represents three types of antihistamines generally available: ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlorpheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another H₁ receptor antagonist which may be used in combination with a PDE4 inhibitor.

Examples of preferred anti-histamines include, methapyrilene and loratadine.

The invention thus provides, in a further aspect, a combination comprising a salt of the invention together with a PDE4 inhibitor.

The invention thus provides, in a further aspect, a combination comprising a salt of the invention together with a corticosteroid, e.g. fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester or 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

The invention provides, in a further aspect, a combination comprising a salt of the invention together with an anticholinergic, e.g. ipratropium, oxitropium or tiotropium.

The invention provides, in a further aspect, a combination comprising a salt of the invention together with an antihistamine.

The invention provides, in a further aspect, a combination comprising a salt of the invention together with a PDE4 inhibitor and a corticosteroid, e.g. with an antihistamine and a corticosteroid as described hereinabove.

The invention provides, in a further aspect, a combination comprising a salt of the invention together with an anticholinergic and a PDE-4 inhibitor, e.g. with a PDE4 inhibitor and an anticholinergic as described hereinabove.

The combinations referred to above may conveniently be presented for use in the form of a pharmaceutical formulation and thus pharmaceutical formulations comprising a combination as defined above together with a physiologically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

Figure 1:
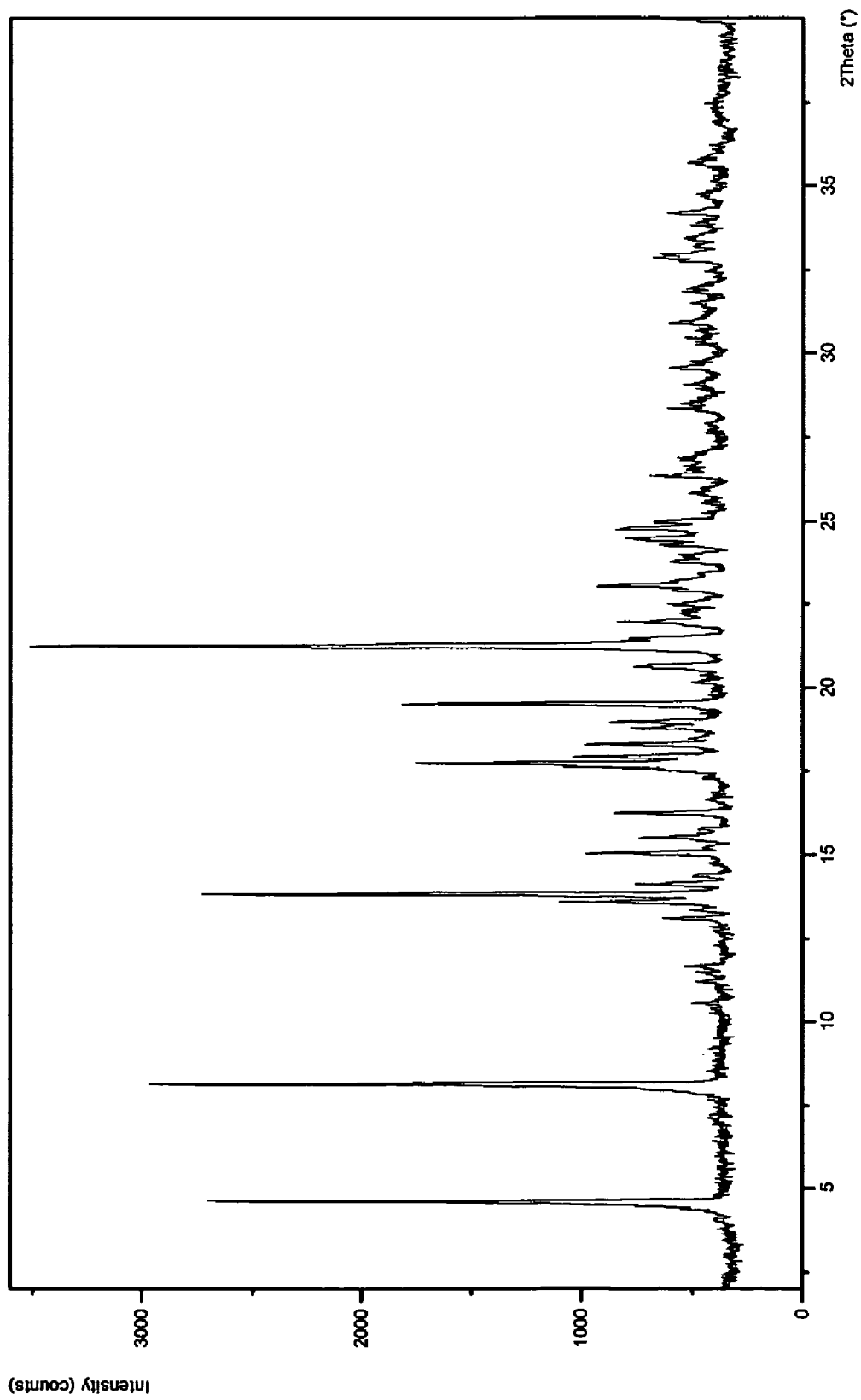
FIG. 1 shows an x-ray powder diffraction pattern of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one cinnamate.

For a better understanding of the invention, the following Examples are given by way of illustration.

ABBREVIATIONS

DMSO Dimethylsulfoxide
DSC Differential scanning calorimetry
H₂O Water
HPLC High pressure liquid chromatography
TGA Thermogravimetric analysis
THF Tetrahydrofuran
TLC Thin layer chromatography
TMS Trimethylsilane
XRPD X-ray powder diffraction
IMS Industrial methylated spirits The following analytical methods were used in respect of Examples 1-6:

XRPD anlaysis was performed on a Panalytical X-ray powder diffractometer, model X'Pert Pro PW3040/60, serial number DY1850. The method runs from 2 to 40 degrees 2-Theta with a 0.0167 degree 2-Theta step size and a 31.75 second collection time at each step using an X'celerator detector.

1H NMR spectra were acquired on a 400 MHz Bruker DPX400 spectrometer. Sample was dissolved in dmso-d6 and chemical shifts were reported in ppm relative to the TMS signal at 0 ppm.

Where necessary reaction mixtures were purified using Biotage packed silica columns.

For Example 1 the differential scanning calorimetry analysis was obtained using a Perkin Elmer Pyris 1, serial number 537N9062304. Samples were weighed into an aluminium pan, an aluminium lid placed on top of the sample and compressed with a brass rod. An empty pan and lid served as reference. Samples were equilibrated at 30° C. and heated at 10° C./min to 300° C. The instrument was calibrated using indium, tin and lead standards.

For Examples 2, 3 and 4, the differential scanning calorimetry analysis was obtained using a TA Instruments 2920 MDSC, serial number M2920-234. Samples were weighed into an aluminium pan, a vented aluminium lid placed on top of the sample and compressed with a brass rod. An empty pan and lid served as reference. Samples were equilibrated at 30° C. and heated at 10° C./min to a temperature between 250 and 350° C. The instrument was calibrated using indium and lead standards.

For Example 1, the thermogravimetric analysis was obtained using a Perkin Elmer Pyris 1, serial number 537N9031106. Samples were placed into a tared aluminium pan and then positioned on a platinum crucible. Samples were heated from 30° C. at 10° C./min to 300° C. The instrument was calibrated for temperature using the Curie point of nickel and alumel.

For Examples 2, 3 and 4, the thermogravimetric analysis was obtained using a TA Instruments 2950 TGA, serial number HA2950-226. Samples were placed into a tared aluminium pan and then positioned on a platinum crucible. Samples were heated from ambient at 10° C./min to a temperature between 250 and 350° C. The instrument was calibrated for temperature using the Curie point of nickel and alumel.

REFERENCE EXAMPLE

Unless noted otherwise, in this reference example reagents, starting material and solvents were purchased from commercial suppliers, for example Sigma-Aldrich (St. Louis, Mo.), J. T. Baker (Phillipsburg, N.J.), and Honeywell Burdick and Jackson (Muskegon, Mich.), and used without further purification; reactions were run under nitrogen atmosphere; reaction mixtures were monitored by thin layer chromatography (silica TLC), analytical high performance liquid chromatography (anal. HPLC), or mass spectrometry; reaction mixtures were commonly purified by flash column chromatography on silica gel, or by preparative HPLC using the general protocol described below; NMR samples were dissolved in deuterated solvent ($CD_3OD$, $CDCl_3$, or DMSO-d6), and spectra were acquired with a Varian Gemini 2000 instrument (300 MHz) under standard parameters; and mass spectrometric identification was performed by an electrospray ionization method (ESMS) with a Perkin Elmer instrument (PE SCIEX API 150 EX).

Synthesis of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one a. Preparation of 4-(2-amino-2-methyl-propoxy)-phenylamine hydrochloride A vigorously stirred slurry of sodium hydride (60% dispersion in mineral oil, 11.32 g, 0.28 mol) in dimethylsulfoxide (400 mL) was heated at 45° C. for 1 h. To this slurry was then added neat 2-amino-2-methyl-1-propanol (25.3 g, 1 equiv). The reaction mixture was warmed to 75° C. for 1 h then cooled to 20° C. in an ice bath. 1-Fluoro-4-nitrobenzene (40 g, 1 equiv) was added slowly, maintaining the temperature below 30° C., and the resulting dark red solution was stirred at room temperature for a further 1 h. The reaction was quenched with water (1000 mL), extracted with dichloromethane (500 mL), and the organic layer washed (1:1 saturated aqueous sodium chloride:water, 1000 mL). The product was precipitated by addition of 3M hydrochloric acid (400 mL) to the organic layer. The resulting orange solid was then filtered and washed with dichloromethane until the filtrate was colourless.

The solid material was immediately transferred to a hydrogenation flask.

Palladium (10% w/w on carbon, 50% w/w water) was added, followed by methanol (500 mL). The slurry was shaken vigorously under 3 atmospheres of hydrogen gas for 16 h. The catalyst was then filtered, the solvent removed under reduced pressure, and the resulting solid dried by azeotroping with toluene (3×150 mL) to afford the title intermediate as a white solid (40 g, 0.18 mol, 65%).

b. Preparation of 5-[(R)-2-(2-{4-[4-(2-amino-2-methyl-propoxy)-phenylamino]-phenyl}-ethylamino)-1-(tert-butyl-dimethyl-silanyloxy)-ethyl]-8-benzyloxy-1H-quinolin-2-one A mixture of the product of step a (23.2 g, 1.1 equiv), 8-benzyloxy-5-{(R)-2-[2-(4-bromo-phenyl)-ethylamino-1-(tert-butyl-dimethyl-silanyloxy)-ethyl}-1H-quinolin-2-one hydrochloride (66.0 g, 0.1 mol), and sodium tert-butoxide (54.0 g, 5.5 equiv) in toluene (600 mL) was stirred at 90° C. until a homogenous solution was obtained. Palladium tris (dibenzylideneacetone) (1.4 g, 0.015 equiv) was added, followed by rac-2,2'-bis(diphenylphosphino)-1,1'-binapthyl (2.87 g, 0.045 equiv). The reaction mixture was stirred at 90° C. for 3 h, then allowed to cool. The solution was washed with water (100 mL), 1:1 saturated aqueous sodium chloride:water (100 mL), then dried over sodium sulfate. The solvent was removed under reduced pressure to afford the title intermediate as a dark brown solid (40 g crude), which was used without further purification.

c. Preparation of 5-[(R)-2-(2-{4-[4-(2-amino-2-methyl-propoxy)-phenylamino]-phenyl}-ethylamino)-1-hydroxy-ethyl]-8-benzyloxy-1H-quinolin-2-one The product of the previous step was treated with triethylamine trihydrofluoride (36 g) in 2-propanol (500 mL)/ethanol (100 mL) at room temperature for 16 h. The mixture was concentrated under reduced pressure to one third of its original volume. 1M aqueous sodium hydroxide (500 mL) was added, followed by acetonitrile (500 mL) and isopropyl acetate (500 mL). The aqueous layer was removed and the organic phase washed with 1:1 saturated aqueous sodium chloride:water (400 mL) then saturated aqueous sodium chloride (400 mL). The organics were dried over sodium sulfate and the solvent removed in vacuo to afford the title intermediate (50 g crude) as a brown solid, which was used without further purification.

d. Synthesis of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one Palladium hydroxide (10 g, 20% w/w on carbon, 50% w/w water) was added to the product from the previous reaction, followed by ethanol (500 mL). The slurry was stirred vigorously under an atmosphere of hydrogen gas for 8 h. The catalyst was filtered and the filtrate concentrated under reduced pressure to afford the title compound (40 g), which was purified by reverse phase HPLC and isolated as its trifluoroacetate salt by lyophilization.

$^1$H NMR (300 MHz, DMSO-d6)

δ (ppm): 10.4 (s, 1H), 9.3 (br s, 1H), 8.7 (br s, 1H), 8.15 (m, 2H), 7.8 (br s, 1H), 7.03 (d, 1H, J=8.2), 6.76-7.01 (m, 10H), 6.42 (d, 1H, J=9.6), 6.1 (br s, 1H), 5.33 (d, 1H, J=9.1), 3.8 (s, 2H), 2.7-3.1 (m, 6H), 1.21 (s, 6H); m/z: [M+H+] calculated for C29H34N4O4, 503.3; found 503.5.

EXAMPLE 1

5-[(R)-2-(2-{4-[4-(2-amino-2-methyl-propoxy)-phenylamino]-phenyl}-ethylamino)-1-hydroxy-ethyl]-8-hydroxy-1H-quinolin-2-one cinnamate (Unquantified Hydrate)

5-[(R)-2-(2-{4-[4-(2-amino-2-methyl-propoxy)-phenylamino]-phenyl}-ethylamino)-1-hydroxy-ethyl]-8-hydroxy-1H-quinolin-2-one (0.11 g) was slurried in aqueous tetrahydrofuran (6:4 THF:$H_2O$ vol/vol, 1.0 mL). Trans-cinnamic acid (0.03 g) in aqueous THF (6:4 THF:$H_2O$ vol/vol 0.1 mL) was made up, most of the acid dissolved. A portion of the acid mixture was added to the free base solution which was seeded with a slurry of the salt in aqueous THF (6:4 THF:$H_2O$ vol/vol). The seed solution had been made by a similar method to this crystallisation. Since a thick slurry did not ensue, the remaining trans cinnamic acid mixture and more seed slurry was added.

Having stirred at room temperature overnight, the slurry was filtered. The filtered solid was washed with aqueous THF (2:1 THF:$H_2O$ vol/vol, 2×0.2 mL) and dried in vacuo at 45° C. overnight to give the title compound.

Yield (not accounting for water content) 63% th

400 MHz NMR in d6-DMSO. TMS as reference at 0 ppm.

δ (ppm): 1.20 (6H) s; 2.62 (2H) t J=7.3 Hz; 2.70-2.85 (4H) m; 3.72 (2H) s; 5.07 (1H) m; 6.50 (1H) d J=15.9 Hz; 6.50 (1H) d J=9.8 Hz; 6.85 (2H) d J=8.6 Hz; 6.87 (2H) d J=9.1 Hz; 6.94 (1H) d J=8.1 Hz; 6.99 (2H) d J=8.8 Hz; 7.00 (2H) d J=8.3 Hz; 7.06 (1H) d J=8.1 Hz; 7.31-7.42 (4H) m; 7.57-7.61 (2H) m; 7.76 (1H) s; 8.18 (1H) d J=10.0 Hz DSC: The sample exhibits an endotherm with an onset of around 60° C. This is followed by a second endotherm with an onset of 106° C. and a subsequent decomposition.

TGA: The sample exhibits a weight loss of 2.8% w/w from ambient to approximately 63° C. This is followed by a second weight loss of 5.4% w/w from 63° C. to approximately 108° C. Subsequent weight loss is due to decomposition.

XRPD analysis of the product is shown in FIG. 1

EXAMPLE 2

5-[(R)-2-(2-{4-[4-(2-amino-2-methyl-propoxy)-phenylamino]-phenyl}-ethylamino)-1-hydroxy-ethyl]-8-hydroxy-1H-quinolin-2-one 4-methoxy cinnamate (Unquantified Hydrate)

5-[(R)-2-(2-{4-[4-(2-amino-2-methyl-propoxy)-phenylamino]-phenyl}-ethylamino)-1-hydroxy-ethyl]-8-hydroxy-1H-quinolin-2-one (0.101 g) was slurried in aqueous tetrahydrofuran (1:1 THF:H$_2$O vol/vol, 1.2 mL). 4-Methoxycinnamic acid (0.036 g, predominantly trans) was added to the mixture. A solution formed before crystallisation spontaneously occurred. The resultant slurry was stirred overnight at room temperature and then filtered. The filtered solid was washed with aqueous tetrahydrofuran (1:1 THF:H$_2$O vol/vol, 3×0.2 mL) and dried at 45° C. in vacuo overnight to give the title compound.

Yield (not accounting for water content) 69% th, 96% w/w
400 MHz NMR in d6-DMSO. TMS as reference at 0 ppm.
δ (ppm): 1.17 (6H) s; 2.61 (2H) t J=7.09 Hz; 2.69-2.83 (4H) m; 3.69 (2H) s; 3.78 (3H) s; 5.05 (1H) m; 6.36 (1H) d J=15.9 Hz; 6.49 (1H) d J=10.0 Hz; 6.85 (2H) d J=8.1 Hz; 6.87 (2H) d J=7.8 Hz; 6.91-7.02 (7H) m; 7.06 (1H) d J=8.1 Hz; 7.41 (1H) d J=15.9 Hz; 7.56 (2H) d J=8.6 Hz; 7.72 (1H) s; 8.18 (1H) d J=10.0 Hz.

DSC: The sample shows an endothermic event with an onset of around 112° C. followed by decomposition.

TGA: The sample exhibits a weight loss of 5.7% w/w from ambient to approximately 125° C. This is followed by a second weight loss of 2.3% w/w from 125° C. to approximately 170° C. due to decomposition.

Figure 2:
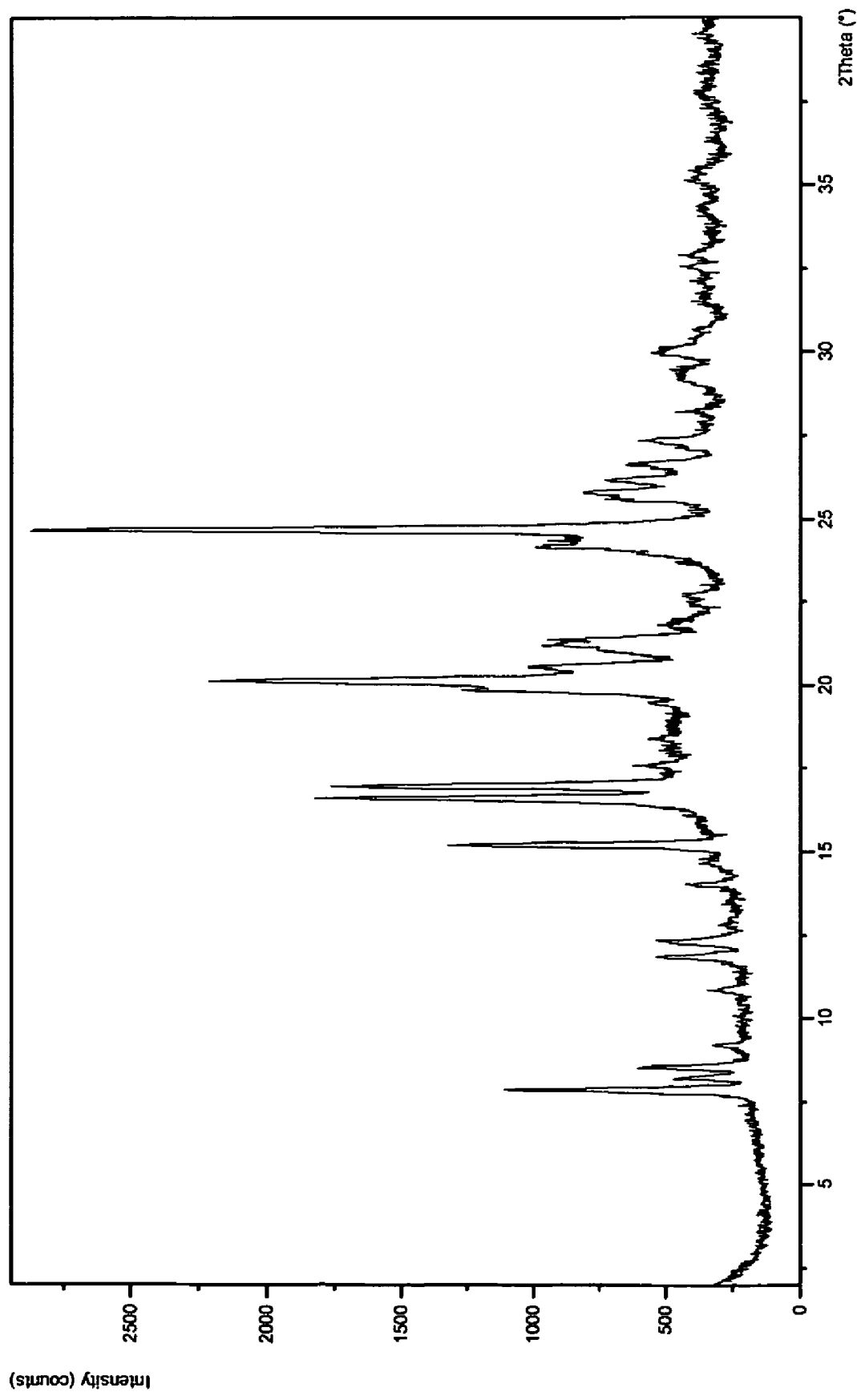
FIG. 2 shows an x-ray powder diffraction pattern of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one 4-methoxycinnamate.

XRPD analysis of the product is shown in FIG. 2

EXAMPLE 3

5-[(R)-2-(2-{4-[4-(2-amino-2-methyl-propoxy)-phenylamino]-phenyl}-ethylamino)-1-hydroxy-ethyl]-8-hydroxy-1H-quinolin-2-one Di-(4-phenylcinnamate) (Unquantified Hydrate)

5-[(R)-2-(2-{4-[4-(2-amino-2-methyl-propoxy)-phenylamino]-phenyl}-ethylamino)-1-hydroxy-ethyl]-8-hydroxy-1H-quinolin-2-one (0.108 g) was slurried in aqueous tetrahydrofuran (1:1 THF:H$_2$O, 1.2 mL). 4-Phenylcinnamic acid (0.049) was added to the stirred mixture at room temperature and spontaneous crystallisation occurred. The mixture was stirred for over 1 hour and then filtered. The filtered solid was washed with aqueous tetrahydrofuran (1:1 THF:H$_2$O, 2×0.2 mL). Having been left to sit at ambient conditions for several hours, the wet solid was dried overnight at 60° C. in vacuo to give the title compound.

Yield (based on free base input, not accounting for water content)=33% th, 62% w/w Yield (based on acid, not accounting for water content)=66% th
400 MHz NMR in d6-DMSO. TMS as reference at 0 ppm.
δ (ppm): 1.23 (6H) s; 2.65 (2H) t J=7.3 Hz; 2.75-2.88 (4H) m; 3.76 (2H) s; 5.10 (1H) m; 6.50 (1H) d J=9.8 Hz; 6.56 (2H) d J=15.9 Hz; 6.86 (2H) d J=8.6 Hz; 6.88 (2H) d J=9.1 Hz; 6.96 (1H) d J=8.1 Hz; 6.99 (2H) d J=8.8 Hz; 7.00 (2H) d J=8.8 Hz; 7.07 (1H) d J=8.1 Hz; 7.38 (2H) t J=7.3 Hz; 7.45-7.49 (4H) m; 7.51 (2H) d J=10.3 Hz; 7.67-7.77 (13H) m; 8.19 (1H) d J=10.0 Hz.

DSC: The sample shows an endothermic event with an onset of around 60° C. This is followed by a second endotherm with an onset of 145° C. and subsequent decomposition.

Figure 3:
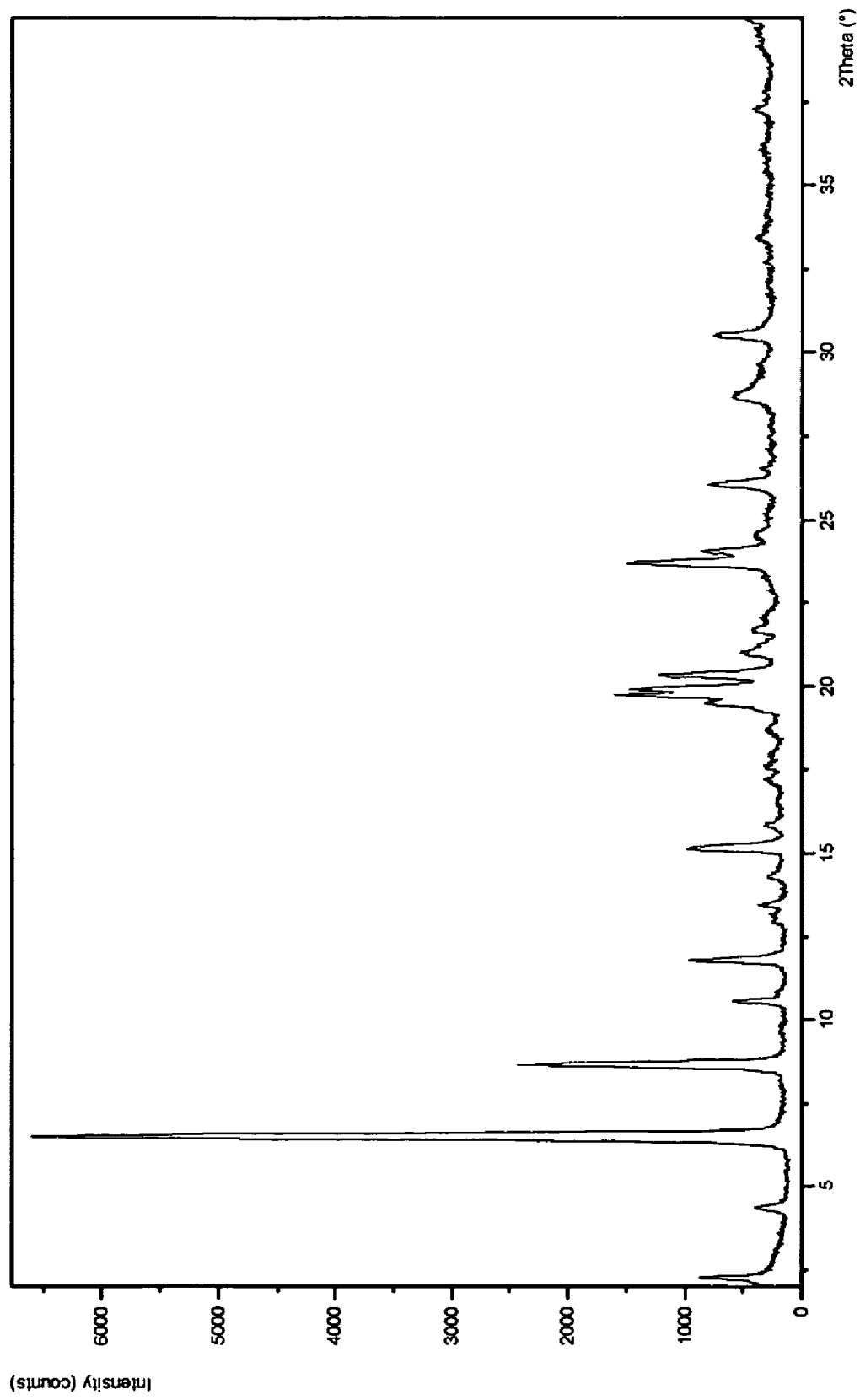
FIG. 3 shows an x-ray powder diffraction pattern of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one di-(4-phenylcinnamate).

XRPD analysis of the product is shown in FIG. 3

EXAMPLE 4

5-[(R)-2-(2-{4-[4-(2-amino-2-methyl-propoxy)-phenylamino]-phenyl}-ethylamino)-1-hydroxy-ethyl]-8-hydroxy-1H-quinolin-2-one 4-methyl cinnamate Method 1

5-[(R)-2-(2-{4-[4-(2-amino-2-methyl-propoxy)-phenylamino]-phenyl}-ethylamino)-1-hydroxy-ethyl]-8-hydroxy-1H-quinolin-2-one (0.21 g) was dissolved in a mixture of tetrahydrofuran (1.2 mL) and water (1.2 mL). 4-methyl cinnamic acid (0.07 g, predominantly trans) was added to the stirred solution at room temperature and it dissolved. After approximately 10 minutes, crystallisation occurred. The slurry was stirred overnight and filtered. The cake was washed with aqueous Tetrahydrofuran (1:1 THF:water, 2×0.4 mL, 1×0.2 mL) to afford the title compound which was dried overnight under vacuum at 45° C.

400 MHz NMR in D6-DMSO. D5-DMSO as reference at 2.5 ppm.

δ (ppm): 1.22 (6H) s; 2.30 (3H) s; 2.64 (2H) t J=6.6 Hz; 2.72-2.86 (4H) m; 3.74 (2H) s; 5.09 (1H) m; 6.43 (1H) d J=15.9 Hz; 6.49 (1H) d J=10.0 Hz; 6.86 (4H) m; 6.93-7.03 (5H) m; 7.06 (1H) d J=7.8 Hz; 7.17 (2H) d J=7.8 Hz; 7.34 (1H) d J=15.9 Hz; 7.45 (2H) d J=7.8 Hz; 7.75 (1H) s; 8.19 (1H) d J=10.0 Hz Expected yield 75% th, 100% w/w DSC: The sample shows an endothermic event with an onset of around 106° C. This is followed by decomposition.

TGA: The sample exhibits a weight loss of 6.1% w/w from ambient to approximately 120° C. This is followed by a second weight loss of 2.0% w/w and decomposition.

Figure 4:
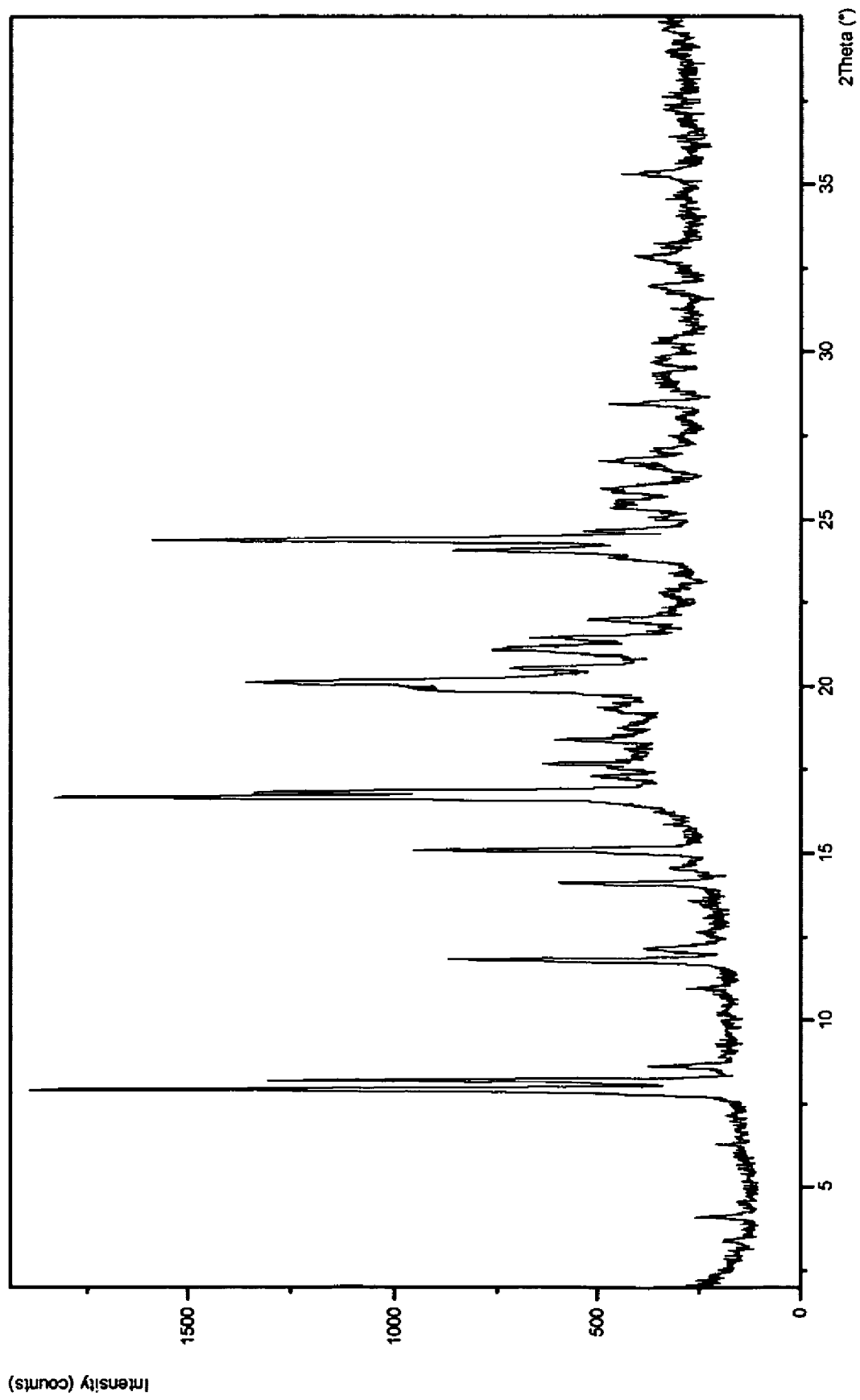
FIG. 4 shows an x-ray powder diffraction pattern of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one 4-methylcinnamate (prepared according to the method of Example 4, Method 1)

The XRPD pattern of this product is shown in FIG. 4.

Method 2

5-[(R)-2-(2-{4-[4-(2-amino-2-methyl-propoxy)-phenylamino]-phenyl}-ethylamino)-1-hydroxy-ethyl]-8-hydroxy-1H-quinolin-2-one (17.77 g) was dissolved in a mixture of tetrahydrofuran (89 mL) and water (89 mL). 4-methyl cinnamic acid (6.02 g, predominantly trans) was weighed out and about ¼ was added to the free base solution followed by some seed crystals. The mixture was stirred and the remaining acid was added in portions over the following 1½ hours. After a further 4 hours stirring, the slurry was filtered. The cake was washed with aqueous tetrahydrofuran (1:1 THF:water, 36 mL) and then tetrahydrofuran (2×18 mL) to afford the title compound which was dried overnight at 40-50° C. under vacuum.

400 Mhz NMR in CD$_3$OD. TMS as 0 ppm reference.

δ (ppm): 1.39 (6H) s; 2.32 (3H) s; 2.79 (2H) t J=7.2 Hz; 2.92-3.03 (4H) m; 3.87 (2H) s; 5.25 (1H) d of d J=3.9 and 8.8 Hz; 6.44 (1H) d J=15.9 Hz; 6.63 (1H) d J=9.8 Hz; 6.86-6.93 (4H) m; 6.96 (1H) d J=8.3 Hz; 6.99-7.05 (4H) m; 7.15 (2H) d J=7.8 Hz; 7.19 (1H) d J=8.3 Hz; 7.36 (1H) d J=15.9 Hz; 7.38 (2H) d J=7.6 Hz; 8.34 (1H) d J=9.8 Hz Expected yield: 67% th, 95% w/w DSC: The sample shows an endothermic event with an onset of around 67° C. This is followed by second endotherm with an onset of around 113° C. and then decomposition.

TGA: The sample exhibits a weight loss of 3.7% w/w from ambient to approximately 75° C. This is followed by a second weight loss of 5.1% w/w from 75 to approximately 125° C., a third weight loss of 2.1% w/w and decomposition.

Figure 5:
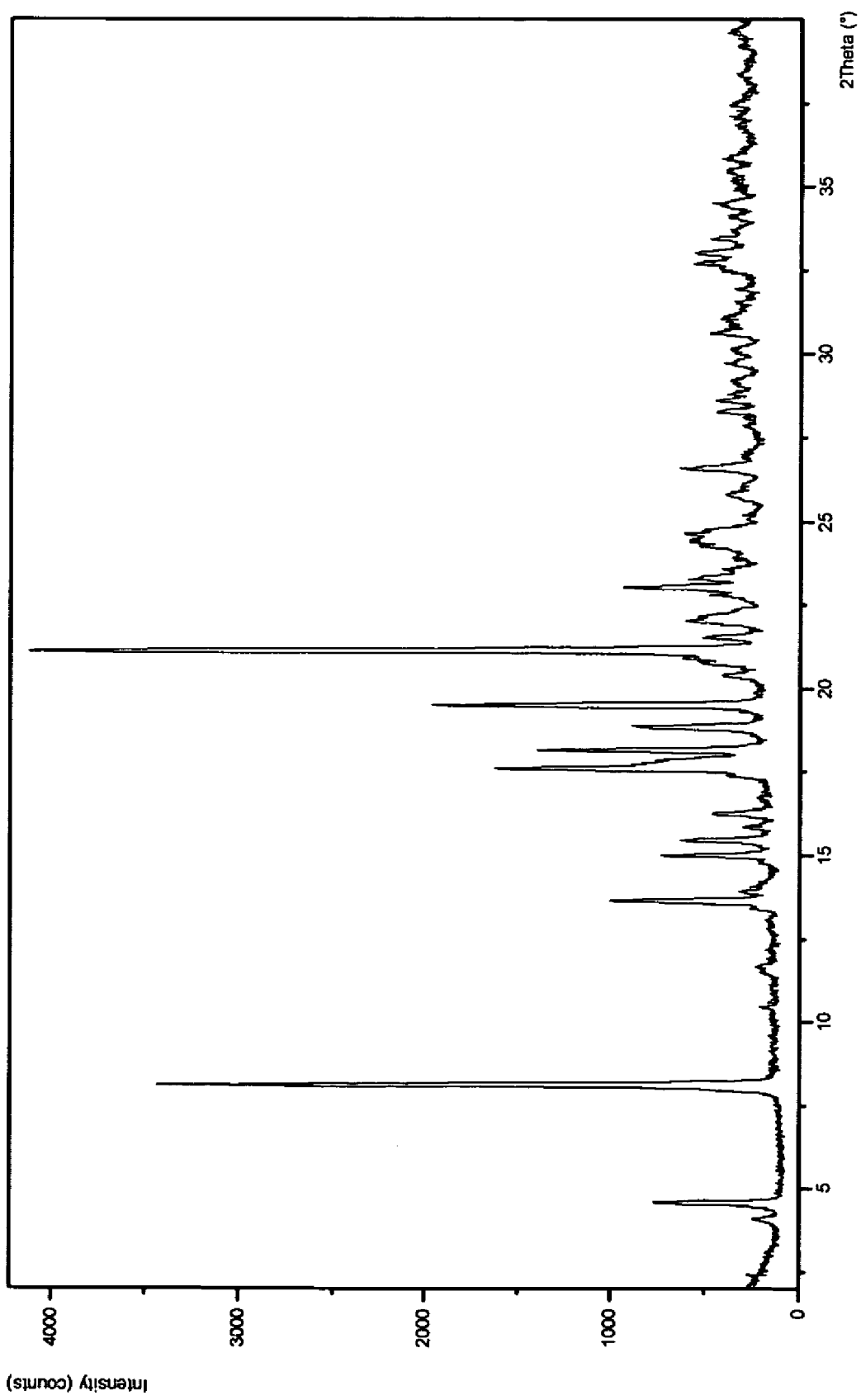
FIG. 5 shows an x-ray powder diffraction pattern of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one 4-methylcinnamate (prepared according to the method of Example 4, Method 2).

The XRPD pattern of this product is shown in FIG. 5.

EXAMPLE 5

(a) Formation of 3.5 hydrate of 4-methyl cinnamate Salt

4-Methyl cinnamic acid (33.7 g, 0.85 eq) was added to a solution of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one free base (which may be prepared according to the method of Ex 6(d)) in aqueous IMS. The mixture was seeded but the seed dissolved. Water (3×50 mL, 3×0.34 vols) was added until seeding gave a slow crystallisation. After 1.5 hours additional water (50 mL, 0.34 vols) was added and the mixture stirred at room temperature overnight. More water (50 ml, 0.34 vols) was added to the mixture. After 4 hours the slurry was filtered. The cake was washed with 15% vol/vol aqueous IMS (3×150 mL, 3×1 vol), taking the first wash to 'dry land' (no visible liquid on cake) but deliquoring the cake significantly after the remaining two washes. The cake was dried in a vacuum oven at ~100 mbar at 43° C. for approximately 24 hours to afford the title compound (127 g), Yield 71% th, 88% w/w The XRPD of the product matches that shown previously in FIG. 5.

(b) 4-Methyl cinnamate dihydrate 4-methyl cinnamate 3.5 hydrate (134.9 g), prepared by the above method, was further dried in a vacuum oven at 40° C. with a vacuum pump to reduce to significantly below 100 mbar. Most of the resulting solid (67.7 g) was slurried in 5% vol/vol aqueous IMS (500 mL, 7.4 vols) for 7 hours. The slurry was filtered and the cake washed with 5% vol/vol aqueous IMS (70 mL×2, 2×1 vol). The cake was dried in a vacuum oven (42° C., ~100 mbar) overnight to afford the title compound (61.8 g).

Yield from 3.5 hydrate 90% th, 86% w/w

XRPD of the product matches that shown previously in FIG. 4.

EXAMPLE 6

Alternative Synthesis of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one a. {1,1-dimethyl-2-[(4-nitrophenyl)oxy]ethyl}amine A solution of 2-amino-2-methyl-1-propanol (488 g, 5.47 mol) in tetrahydrofuran (1.46 L) was added over 35 mins to a solution of potassium tert-butoxide (634 g, 5.65 mol) in tetrahydrofuran (2.95 L) at 2±3° C. The mixture was maintained at this temperature for a further 55 minutes before 4-fluoronitrobenzene (551 mL, 3.90 mol) was added over 1 hour 25 mins keeping the temperature below 10° C. The mixture was warmed to 20±3° C. and stirred for 2 hours. Water (1.95 L) and Isopropyl acetate (1.95 L) were charged to the mixture which was stirred, settled and separated. The organic phase was washed again with water (1.95 L) before 5M hydrochloric acid (1.95 L) was charged, keeping the temperature below 25° C. Isooctane (1.95 L) was added and the layers separated. 5M hydrochloric acid (322 mL) was added to the aqueous phase which was then reduced to approximately 3.9 L by vacuum distillation, causing spontaneous crystallisation, and stirred at room temperature overnight. Filtration, washing with water (2×488 mL) and drying in vacuo at around 48° C. afforded the title intermediate as a white solid (972.1 g, 72% th).

b. {4-[(2-amino-2-methylpropyl)oxy]phenyl}amine dihydrochloride

{1,1-dimethyl-2-[(4-nitrophenyl)oxy]ethyl}amine (752.5 g, 3.05 mol), 5% Pd/C (Escat 160, 30.1 g, 53.6% w/w water, 6.6 mmol Pd) and IMS (6.0 L) were stirred under hydrogen at atmospheric pressure until the exotherm ceased. The catalyst was filtered off through a CUNO celite filter which was washed with IMS (3.0 L). Concentrated hydrochloric acid (300 mL) was added to the combined organic solution over 45 minutes giving rise to a slurry which was stirred at room temperature overnight. Filtration, washing of the cake with IMS (2×1.12 L) and drying in vacuo at 37° C. afforded the title intermediate as a pink solid (646 g, 84% th).

c 5-[(R)-2-(2-{4-[4-(2-amino-2-methyl-propoxy)-phenylamino]-phenyl}-ethylamino)-1-(tert-butyl-dimethyl-silanyloxy)-ethyl]-8-benzyloxy-1H-quinolin-2-one 1,4-Dioxane (4.33 L) was added to a mixture of {4-[(2-amino-2-methylpropyl)oxy]phenyl}amine dihydrochloride (406.7 g, 1.61 mol), 8-benzyloxy-5-{(R)-2-[2-(4-bromophenyl)-ethylamino-1-(tert-butyl-dimethyl-silanyloxy)-ethyl}-1H-quinolin-2-one hydrochloride (865.4 g, 1.34 mol), sodium tert-butoxide (900 g, 9.36 mol), bis(dibenzylideneacetone)palladium (9.4 g) and BINAP (rac-2,2'-bis(diphenylphosphino)-1,1'-binapthyl, 15.58 g). The mixture was stirred and heated at 87±3° C. for 4 hours. The mixture was cooled to room temperature, quenched with water (2.60 L) and passed through a CUNO zetacarbon filter. Methyl acetate (2.60 L) and saturated sodium chloride solution (made with 1.66 L water) were added, the solution mixed and the phases settled and separated. The organic phase was washed with sodium chloride solution (623 g in 2.84 L water). Methanol (3.46 L) and concentrated hydrochloric acid (735.6 mL) were added to the reaction mixture which was heated to 50±3° C. for 17 hours before returning to 20±3° C. 5M sodium hydroxide solution (3.46 L) methyl acetate (3.46 L) and saturated brine (made with 1.1 L water) were added, the mixture stirred and the layers separated. The organic phase was washed with sodium chloride solution (622.8 g in 2.84 L water) and evaporated to a dark foam on a rotary evaporator (851.2 g, crude yield 107% th, 98% w/w).

The foam was redissolved in methanol (1.2 L). A portion of the solution (1069 g) that contained 500 g of the crude material was injected onto a column in a biotage flash 150 system and eluted isocratically (99 parts methanol, 1 part 2M ammonia in methanol). The product containing fractions were grouped by purity, clean fractions and those with low level impurities were combined and evaporated to give the title compound as 2 yellow foams (combined mass 305.6 g, 0.51 mol, yield from 8-benzyloxy-5-{(R)-2-[2-(4-bromo-phenyl)-ethylamino-1-(tert-butyl-dimethyl-silanyloxy)-ethyl}-1H-quinolin-2-one hydrochloride, 65% th)

d. Synthesis of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one 5-[(R)-2-(2-{4-[4-(2-amino-2-methyl-propoxy)-phenylamino]-phenyl}-ethylamino)-1-(tert-butyl-dimethyl-silanyloxy)-ethyl]-8-benzyloxy-1H-quinolin-2-one (145 g 0.24 mol), made and purified in a similar way to that described in section c above, palladium hydroxide on carbon (29 g 20% w/w Pd on dry basis, wet) and IMS (1.075 L) were stirred under hydrogen at atmospheric pressure and heated with a water bath at 45° C. for a total of 11.5 hours (over 2 days). The catalyst was filtered off on a bed of celite which was twice with IMS (300 mL then 150 mL) and then with aqueous IMS (2:1 IMS:water, 150 mL). This aqueous alcoholic free base solution could then be used directly for salt formation or dried and evaporated to give a solid which could be re-dissolved for salt formation.

What is claimed is:

1. A 4-methyl cinnamate salt of the compound of formula (I):

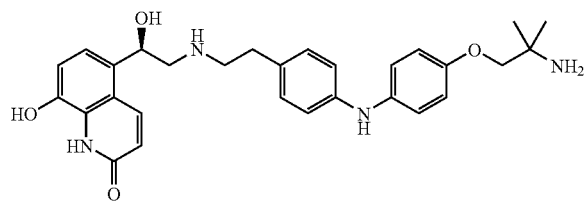

having the chemical name 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

2. A crystalline form of the salt of 5-[(R)-2-(2-{4-[4-(2-amino-2-methyl  -propoxy)-phenylamino]-phenyl}-ethylamino)-1-hydroxy-ethyl]-8-hydroxy-1H-quinolin-2-one, wherein the crystalline salt is selected from the group consisting of cinnamate, 4-methoxycinnamate, di-(4-phenylcinnamate) and 4-methyl cinnamate salt.

3. The crystalline form of the salt according to claim 2, wherein the crystalline salt is 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one cinnamate.

4. The crystalline form of the salt according to claim 2, wherein the crystalline salt is 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one 4-methoxy cinnamate.

5. The crystalline form of the salt according to claim 2, wherein the crystalline salt is 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one di-(4-phenyl cinnamate).

6. A pharmaceutical formulation comprising a salt of the compound according to claim 1, and a pharmaceutically acceptable carrier or excipient, and optionally one or more other therapeutic ingredients.

7. A combination comprising a salt of the compound according to claim 1 and one or more other therapeutic ingredients.

8. A pharmaceutical formulation comprising a crystalline form of the salt according to claim 2, and a pharmaceutically acceptable carrier or excipient, and optionally one or more other therapeutic ingredients.

9. A combination comprising a crystalline form of the salt according to claim 2 and one or more other therapeutic ingredients.

10. A method for the treatment of a disease associated with reversible airways obstruction selected from the group consisting of asthma and chronic obstructive pulmonary disease (COPD) in a mammal, which comprises administrating a therapeutically effective amount of a compound according to claim 1.

11. The method according to claim 10, wherein the mammal is a human.

12. A method for the treatment of a disease associated with reversible airways obstruction selected from the group consisting of asthma and chronic obstructive pulmonary disease (COPD) in a mammal which comprises administrating a therapeutically effective amount of a compound according to claim 2.

13. The method according to claim 12, wherein the mammal is a human.

14. A method for preparing a crystalline compound according to claim 1 which method comprises contacting in solution 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one with 4-methylcinnamic acid.

15. The method according to claim 10, wherein the disease associated with reversible airways obstruction is asthma.

16. The method according to claim 10, wherein the disease associated with reversible airways obstruction is COPD.

17. The method according to claim 12, wherein the disease associated with reversible airways obstruction is asthma.

18. The method according to claim 12, wherein the disease associated with reversible airways obstruction is COPD.

* * * * *